United States Patent
Daignault, Jr.

(10) Patent No.: US 7,928,995 B2
(45) Date of Patent: *Apr. 19, 2011

(54) SYSTEM FOR REGIONAL DATA ASSOCIATION AND PRESENTATION AND METHOD FOR THE SAME

(75) Inventor: Richard J Daignault, Jr., Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/710,398

(22) Filed: Feb. 23, 2010

(65) Prior Publication Data

US 2010/0141676 A1 Jun. 10, 2010

Related U.S. Application Data

(63) Continuation of application No. 12/106,954, filed on Apr. 21, 2008, now Pat. No. 7,671,874, which is a continuation of application No. 10/659,763, filed on Sep. 9, 2003, now Pat. No. 7,362,334, which is a continuation of application No. 09/587,920, filed on Jun. 5, 2000, now Pat. No. 6,690,397.

(51) Int. Cl.
*A61B 19/00* (2006.01)
*G09G 5/00* (2006.01)
*G06F 17/00* (2006.01)
*G06F 15/00* (2006.01)
*G06F 3/48* (2006.01)
*A61N 1/00* (2006.01)
*A61N 1/34* (2006.01)

(52) U.S. Cl. ........ 345/619; 345/156; 345/603; 348/441; 348/469; 600/557; 707/1; 707/100; 707/103; 715/700; 715/764

(58) Field of Classification Search .................. None
See application file for complete search history.

(56) References Cited

U.S. PATENT DOCUMENTS

| 4,274,140 A | 6/1981 | Watson |
| 4,672,559 A | 6/1987 | Jansson et al. |
| 4,770,182 A | 9/1988 | Damadian et al. |
| 5,121,470 A | 6/1992 | Trautman |
| 5,319,720 A | 6/1994 | Yokoyama et al. |
| 5,370,672 A | 12/1994 | Fowler et al. |
| 5,371,778 A | 12/1994 | Yanof et al. |
| 5,443,486 A | 8/1995 | Hrdlicka et al. |

(Continued)

FOREIGN PATENT DOCUMENTS

EP 0811395 12/1997

(Continued)

OTHER PUBLICATIONS

US, International Preliminary Examination Report for PCT/US01/17710 dated Oct. 15, 2003.

(Continued)

*Primary Examiner* — Wesner Sajous
(74) *Attorney, Agent, or Firm* — Christopher S. L. Crawford; Peter Lando; Melissa Acosta

(57) ABSTRACT

A database methodology that concerns the mapping of any arbitrary object into a plurality of regions, enabling the assignment of multiple region-specific attributes thereto and facilitating the concurrent, graphical presentation of any assigned attributes. Attribute storage, manipulation, and presentation are driven by the individual regions and characteristics of the object.

11 Claims, 8 Drawing Sheets

U.S. PATENT DOCUMENTS

| | | |
|---|---|---|
| 5,452,416 A | 9/1995 | Hilton et al. |
| 5,619,631 A | 4/1997 | Schott |
| 5,627,979 A | 5/1997 | Chang et al. |
| 5,692,500 A | 12/1997 | Gaston-Johansson |
| 5,729,731 A | 3/1998 | Yajima et al. |
| 5,734,888 A | 3/1998 | Li et al. |
| 5,790,121 A | 8/1998 | Sklar et al. |
| 5,803,914 A | 9/1998 | Ryals et al. |
| 5,841,437 A | 11/1998 | Fishkin et al. |
| 5,850,206 A | 12/1998 | Kashiwagi |
| 5,872,859 A | 2/1999 | Gur et al. |
| 5,878,746 A | 3/1999 | Lemelson et al. |
| 5,891,030 A | 4/1999 | Johnson et al. |
| 5,909,217 A | 6/1999 | Bereiter |
| 5,912,674 A | 6/1999 | Magarshak |
| 5,915,262 A | 6/1999 | Bridgers et al. |
| 5,938,690 A | 8/1999 | Law et al. |
| 5,960,448 A | 9/1999 | Reichek et al. |
| 5,982,383 A | 11/1999 | Kumar et al. |
| 5,984,368 A | 11/1999 | Cain |
| 5,991,429 A | 11/1999 | Coffin et al. |
| 5,999,192 A | 12/1999 | Selfridge et al. |
| 6,018,346 A | 1/2000 | Moran et al. |
| 6,031,929 A | 2/2000 | Maitz et al. |
| 6,031,935 A | 2/2000 | Kimmel |
| 6,119,185 A | 9/2000 | Westerinen et al. |
| 6,285,842 B1 | 9/2001 | Katamoto et al. |
| 6,377,288 B1 | 4/2002 | Moran et al. |
| 6,690,397 B1 * | 2/2004 | Daignault, Jr. ................ 715/764 |
| 7,092,569 B1 | 8/2006 | Kinjo |
| 7,362,334 B2 * | 4/2008 | Daignault, Jr. ................ 345/581 |
| 7,671,874 B2 * | 3/2010 | Daignault, Jr. ................ 345/619 |
| 2002/0032385 A1 | 3/2002 | Raymond et al. |
| 2002/0086343 A1 | 7/2002 | Cameron et al. |
| 2003/0004925 A1 * | 1/2003 | Knoblock et al. ................ 707/1 |
| 2003/0215134 A1 | 11/2003 | Krumm |
| 2004/0059395 A1 | 3/2004 | North et al. |
| 2004/0087839 A1 | 5/2004 | Raymond et al. |
| 2005/0240605 A1 * | 10/2005 | Knoblock et al. ............ 707/100 |

FOREIGN PATENT DOCUMENTS

| | | |
|---|---|---|
| WO | WO 0139831 | 6/2001 |

OTHER PUBLICATIONS

EPO, Examination Report for EP 01939808.0 dated Jul. 1, 2008.

Neuez, Gael, "Pain Mapping: Details", XP002907280, p. 1-5.

* cited by examiner

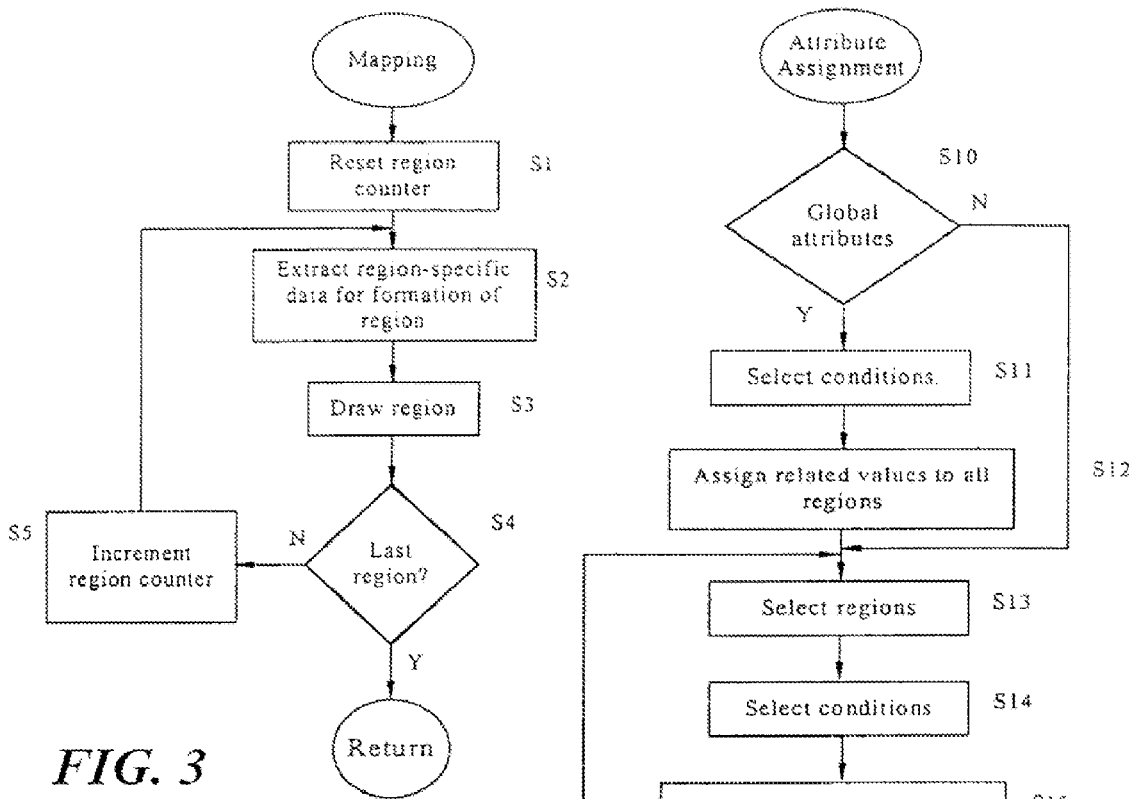
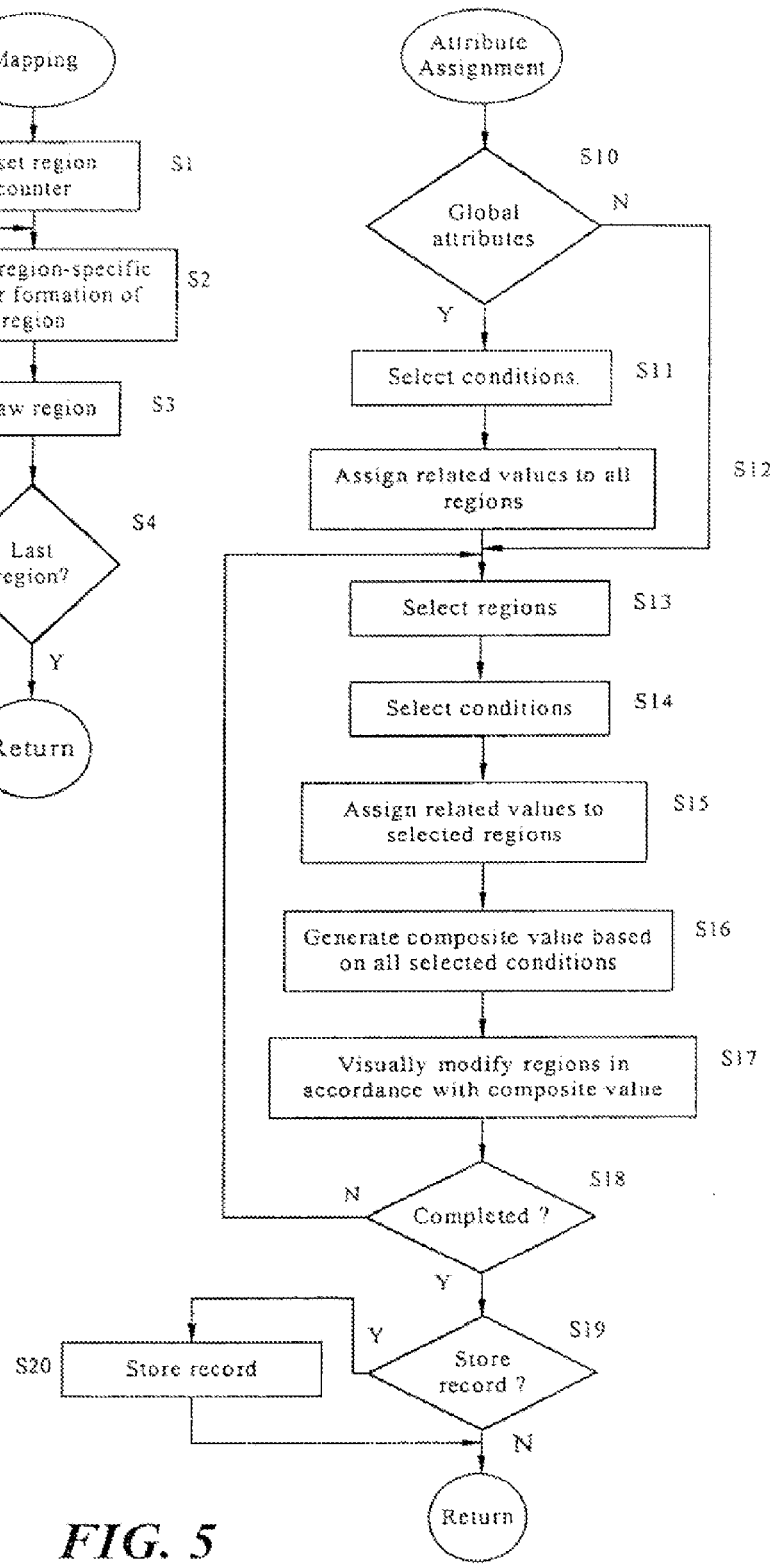
FIG. 3
FIG. 5

SYSTEM FOR REGIONAL DATA ASSOCIATION AND PRESENTATION AND METHOD FOR THE SAME

BACKGROUND OF THE INVENTION

Traditionally, patients suffering from pain (e.g., chronic pain) have been limited to verbal characterizations and/or simple hand-rendered drawings to identify such critical information as the location, the nature, and the severity of their pain. Of course, such characterizations can vary in as many ways as there are people to convey such information. Thus, consistent assessment, diagnosis, and treatment of like conditions have been historically problematic.

Unfortunately, the introduction of computers and other digital devices to this area has not lessened the burden on the patient. Moreover, the qualitative value of information from these devices has not substantively improved. Specifically, such computers and other digital devices function similarly to traditional pen and paper. The user, whether patient or physician, is presented an outline, for example, of the human body, and is then asked to draw, circle, or otherwise indicate the pain-afflicted bodily regions. To this end, reference is made to FIG. 1, which represents but one example of such a user-interface for these conventional systems.

It is acknowledged that known "electronic" systems offer some improved functionality. In particular, data entry from one patient to another is inherently harmonized, as the patients are constrained by a limited number of options in characterizing his/her pain. Moreover, data storage is improved, as the visual images can be readily transmitted as well as stored on long-term and/or transportable storage media.

However, in the context of these known systems, supplied data is typically accepted at a pixel-level basis. Because the resolution of the representations (FIG. 1) must typically be great, the size of each data input is significant. Accordingly, for any measurable number of patients, a considerable amount of storage space is required, thus adversely affecting a practitioner's ability to establish a statistically relevant database. Further yet, searches or comparisons of such data can be hindered by the significant quantity of data that can exist (and must be managed) for a given representation.

For purposes of spinal cord stimulation (SCS), or the controlled application of specific electrical energy to certain spinal nervous tissue to manage the transmission of specialized pain signals through such tissue, it is recognized that some conventional systems correlate pixel-level "pain" data to pre-determined "dermatome" regions for purposes of presentation. For purposes of explanation, pain representations 102 drawn on a graphical image of a human figure (e.g., FIG. 1) are converted to correspond to specific dermatomes 102' of FIG. 2.

Dermatomes are recognized exterior regions of the human body that are respectively associated with certain spinal nerve roots at particular longitudinal spinal positions. Particularly, the head and neck regions are associated with C2-C8; the back regions extends from C2-S3; the central diaphragm is associated with spinal nerve roots between C3 and C5; the upper extremities are correspond to C5 and T1; the thoracic wall extends from T1 to T11; the peripheral diaphragm is between T6 and T11; the abdominal wall is associated with T6-L1; lower extremities are located from L2 to S2; and the perineum from L4 to S4. By example, to address chronic pain sensations that commonly focus on the lower back and lower extremities, a specific energy field can usually be applied to a region between bony level T8 and T10. Correlating "free-form" pain representations 102 to specific dermatomes 102' is intended to assist a practitioner in identifying a longitudinal, vertebral position (i.e., afflicted nervous tissue) that would likely benefit from an application of therapeutic treatment. As can be seen, however, such correlation is not always accurate. As is common practice, the dermatome-related data is neither stored nor otherwise manipulated in this form but rather is generated when needed.

Another negative characteristic of conventional systems is the limited amount (and quality) of pain-related information recorded and considered. In particular, indicating pain relative to a human representation (e.g., FIG. 1) simply provides relative location information. Any pain characteristics are limited to an intensity value, which is entered through a textual-based, numeric input mechanism 100.

Consequently, a need exists for a database system that enables an object, whether predisposed to regional division or not, to be mapped into a plurality of regions, each region being capable of capturing region-specific and/or object-specific data. With such system, users can consistently and reliably enter information attributable to any given region. Using regionally-consistent, similar objects, this system would enable data for any given object to be compared, universally modified, and/or otherwise manipulated among a plurality of sources.

A further need exists for a database system to graphically present, in a concurrent form, potentially multifarious attributes of any one region.

SUMMARY OF THE INVENTION

An object of the present invention is to provide a database structure that operatively overcomes the shortcomings noted above with respect to known systems.

Another object of the present invention is to provide a database methodology that effects a division of a body or structure into a prescribed number of regions, such regions being indexed relative to one another.

Another object of the present invention is to provide a database methodology that is adapted to associate region-unique attributes as well as region-common attributes with regional data records.

Accordingly, one aspect of the present invention is directed to a graphical database. The database includes an object storage portion, a mapping portion, a selection portion, and an attribute assignment portion. In turn, the storage portion operatively stores a predetermined object representation. The mapping portion extracts the object representation from the object storage portion and, graphically, sub-divides the object representation into a plurality of regions, each region representing a data-input field. The selection portion is adapted to allow selection of at least one region of a sub-divided object image, and the attribute assignment portion assigns conditions to selected regions, whereas the conditions include region-specific information. Each region is adapted to receive a plurality of conditions.

Another aspect of the present invention is a method for assigning positional-specific attributes to an object as well as managing such attributes in a graphical database. The steps of such method include providing a graphical object representation, and dividing the object representation into a plurality of sub-regions. Each region is a graphical, data-input field. The method further concerns selecting at least one region for attribute assignment, and selecting an attribute. For a region subject to an attribute, the process further requires modifying such regions graphically in a manner to convey that the selected attribute is associated with the selected regions. At least one region is adapted to convey visually an association with multiple attributes.

Other objects and advantages of the present invention will be apparent to those of ordinary skill in the art having reference to the following specification together with the drawings.

BRIEF DESCRIPTION OF THE DRAWINGS

FIG. 3 is a routine to effect a mapping of an object;

FIG. 5 is a routine to effect an assignment of object-common and region-specific attributes to mapped regions of an object;

DETAILED DESCRIPTION OF THE PREFERRED EMBODIMENTS

Figure 1:
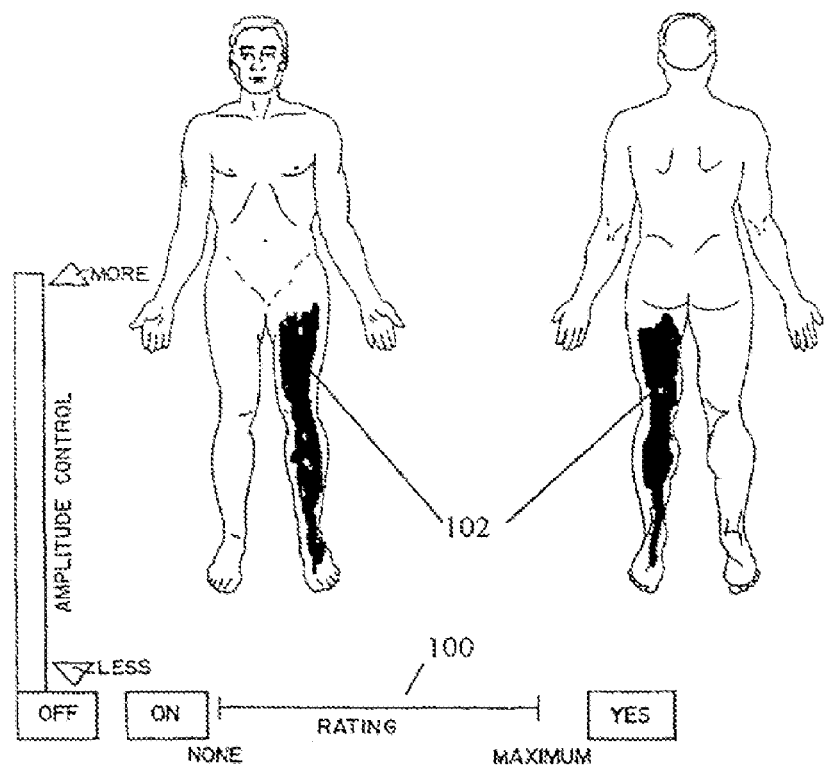
FIG. 1 illustrates a graphical interface for a conventional system that enables entry of pain-related information relative to a predefined object.

Various embodiments, including preferred embodiments, will now be described in detail below with reference to the drawings.

The main components for the system are a general-purpose computer (not shown) and executable software for such computer. The computer is capable of receiving input via its display (i.e., touch screen) or through a mouse or a stylus. While not critical to the invention, the computer preferably operates in a Windows™-based environment. The computer should include, or otherwise be connectable to, a display (or other output device) having sufficient resolution to clearly present the visual information required by the present invention, such information being discussed in greater detail below.

Common to each of the embodiments described herein, the systems of the present invention present a modeled object that is formed of at least two sub-regions. The total number of sub-regions (i.e., "regions") for a given object defines the object in its entirety, and no two regions physically overlap (i.e., in a two-dimensional space). The modeled object can be visually presented in two-dimensions (i.e., greater than three points in a x, y coordinate system) as well as in three-dimensions (i.e., a x, y, z coordinate system).

The number of regions used to model an object is not predefined but rather is selected to provide a sufficient resolution to facilitate the presentation of certain graphical information attributable to each individual region. Of further consideration, the number of regions should further place in context and avoid de-valuing the attributes (or conditions) that are assigned to each region—a concept that will discussed in the context of the individual embodiments below. The regions of a given object are statically defined and fixed positionally relative to adjacent regions and the object boundaries. Regardless, a scaling factor and/or positional offset can be used and applied to all regions equally to adjust a size and/or an orientation of the object as a whole. Preferably, each region is identifiable by a region-specific characteristic, e.g., an alphanumeric designation, a graphical marking, a region boundary shape, or the like.

Demarcating the regions, or "mapping" an object, concerns division of an object into an appropriate number of regions. In this instance, the computer divides the object in a uniform manner based on a predetermined standard or a user-supplied standard or in a non-uniform manner based on a user-supplied standard. In a preferred embodiment, the mapped object is generated each time the object is displayed; however, a mapped object could be stored and displayed as a complete image.

As stated above, any given object can be defined by any appropriate number of regions. However, for the present system to function in an intended manner for purposes of data manipulation and comparison among multiple data sources, each like object must be mapped in an exact manner so as to provide "regional correspondence" between data sources.

FIG. 3 illustrates a flow chart for mapping an object. In Step S1, a region counter that generates a region count is reset. For this example, the region-specific characteristic, which uniquely identifies each region, is a numerical value. In Step S2, data for generating a region corresponds to the present region count is extracted from a memory of the computer. The extracted data corresponds, for example, a position within the object and a shape for the specific region. The subject region is positioned within the object in Step S3, this positioning typically takes the form of drawing the region of the object in accordance with the data extracted in Step S2. The regions are positioned within a fixed boundary—an outline of the object, which along graphically portrays the object. Further to this step, scaling or offsets are universally applied to each region when the object is subjected to any such modification. In Step S4, a determination is made whether any remaining regions are to be added to the object. If yes, Steps S2 through S4 are repeated. If not, the generation routine is completed.

Each region serves as a vehicle to assign or otherwise attribute certain conditions specifically related to that region, whether region-specific or common to the object. Of course, the conditions are a function of the subject matter that a user desires to be attributed to the object, and more particularly, a region of the object. The conditions available to a user are preferably predetermined. When related to a specific region, the conditions (or attributes) are visually represented by graphical descriptions (e.g., patterns, colors, multi-dimensional representations, etc.) and/or textual information.

Figure 4:
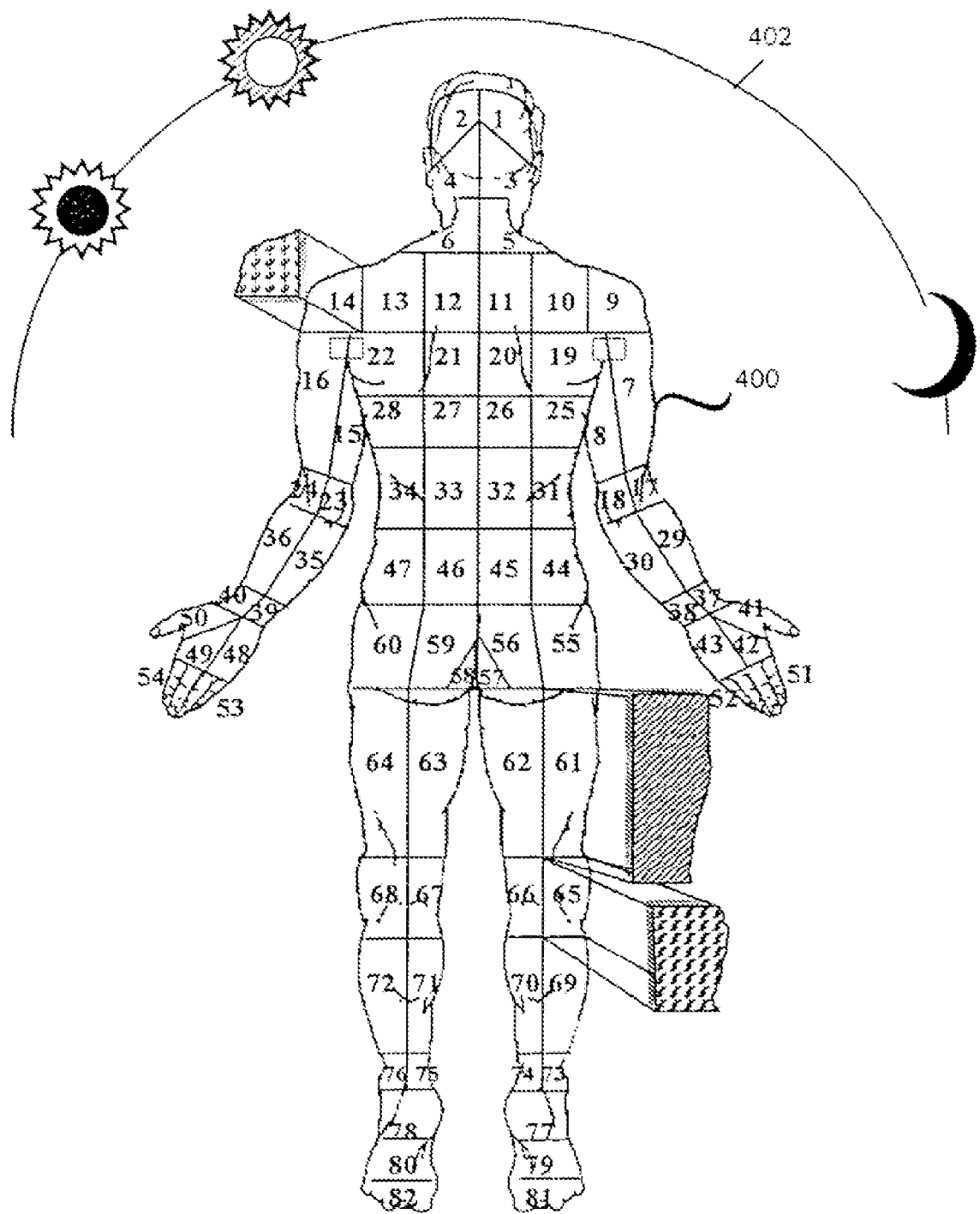
FIG. 4 is a posterior view of an object example in a standing orientation.

For "assigning" a condition to a region, reference is made to FIGS. 4 and 5. In FIG. 4, an object 400 is shown having a plurality of regions 1-82. In this particular illustration, region 14, region 61, and region 65 are shown having particular attributes. Of note, each of the attributes is different—based on different patterns—and distinguishable from the background state of the remaining regions. FIG. 5 shows one technique for assigning different attributes to the regions of an object.

Figure 6:
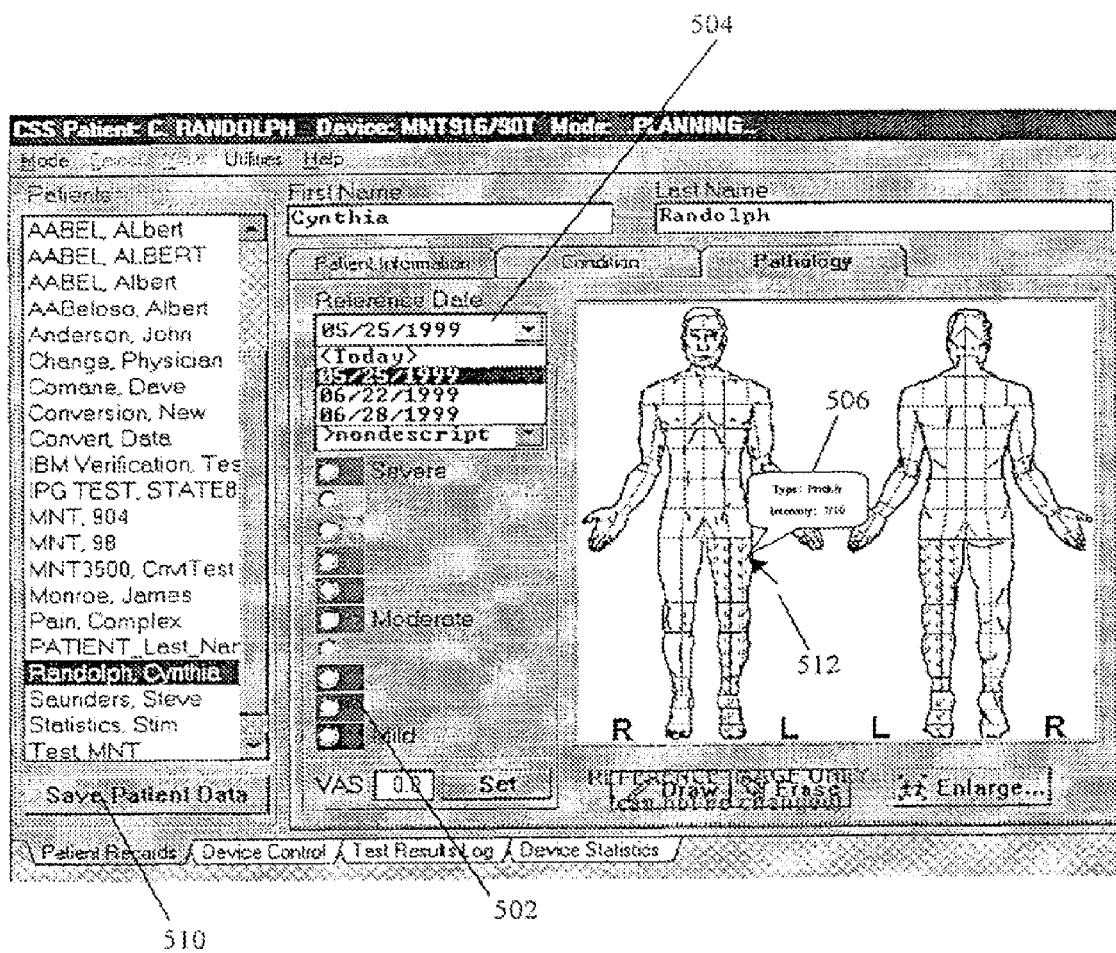
FIG. 6 illustrates an exemplary screen arrangement in accordance with executable software embodying the present invention.

For this operation, an object, e.g., object 400, with its regional subdivisions would be visually presented to a user. The user is offered specific conditions that are a function of the object (e.g., 502 of FIG. 6; 200 and 202 of FIG. 10). The quantity of conditions, assignment of visual properties of such condition, and sequence of attribute access is largely arbitrary. In determining the specific definition of these conditions, one or more of the following actions may prove valuable: providing sufficient definitional variation for the conditions, articulating the visual properties of the conditions based on the resolution of the object (and its regions), and scaling the conditions so that all available conditions are sufficiently displayed simultaneously (FIG. 6). Of further consideration, to enable a proper region-to-region correlation between like objects having like regional mappings, visual properties and sequence of attribute access must remain consistent across such implementations.

In reference to FIG. 5, in Step S10 a decision is made as to whether certain conditions are attributable to all regions. If yes, the user selects one or more conditions (Step S11), and such selected conditions are attributed to all the regions (Step S12). The flow then advances to Step S13.

If the answer to such decision of Step S10 is "no," the user is asked to select one (or more) specific regions (Step S13). The computer recognizes the regions being selected based on (i) a relative position of a virtual pointer with respect to the display or (ii) a peripheral (e.g., touch screen) output signal. With specific regions selected, the user selects one or more conditions attributable to the selected regions (Step S14). Selection of conditions involves "clicking" on graphic representations 502 (FIG. 6; 200 and 202 of FIG. 10) of the available conditions displayed relative to the object and/or entry of textual-related data 508 (FIG. 6).

In Step S16, values representative of the conditions assigned in Steps S12 and S16 are respectively combined into a composite value. While a composite value is not critical to the present invention, the formation of a composite value enables improved data management and control over the "physical" characteristic(s) of the respective region-specific condition values (e.g., length, data arrangement, etc.). Indirectly, controlling the physical characteristic(s) of each regional condition value facilitates additional practical benefits, for example, potentially reducing storage requirements for a plurality of records, providing predictability for storage requirements, and the like.

In Step S17, the regions subject to an assigned condition(s) are graphically altered to convey that certain conditions have been assigned thereto. To illustrate this, reference is made to FIG. 4, where the visual appearances of regions 1, 61, and 65 have been modified. Similarly, the left leg of the human image of FIG. 6 includes a plurality of "modified" regions.

Upon receiving an instruction that data entry is complete (Step S17), the supplied data is subject to being stored (Steps S19 and S20), and the user is then returned to a principal routine, which is generally responsible for effecting execution of the appropriate subroutines.

As an alternative approach to the method described above, Step S13 can be disregarded. In its place, the user could select and "drag" a graphical representation of an applicable condition to an individual, non-selected region or to a group of previously selected regions.

As another alternative, Step S13 can again be disregarded. For this method, once a condition is selected, the user is provided with a virtual drawing implement (i.e., a pointer or the like) when a displayed cursor (or stylus) is positioned relative to regions of the displayed object subject to receiving conditional attributes. The user is then allowed to freely "paint" those regions that may be characterized by the selected condition. The computer then normalizes the input data relative to the regions of the object. Concerning such normalization, the computer graphically compares all "painted" pixels to the underlying pixels that form the regions of the object. The computer compares a percentage of occupation of each affected region to a predetermined threshold value (e.g., 30%). Accordingly, for any given region, if the percentage of occupation exceeds the threshold value, such region as a whole is "selected," and it is attributed the selected condition.

Data storage occurs upon indication by the user, for example, by selecting the "save patient data" option 510 of FIG. 6 (Steps S19 and S20 of FIG. 5). Records are indexed by the object subject (e.g., patient name, geographic location, etc.), and any assigned conditions for such object are recorded on a regional basis as a part of such record. Object-based records (i.e., "object records") include a field for each region, such field being individually identifiable by the respective region-specific characteristics. Within each field, it is possible to store all conditions of the corresponding region. It is further preferable that each field be capable of maintaining previous records concerning conditions (or the lack of conditions) attributable to such field in the past. Likewise, each field may also include links to other supporting databases (i.e., condition indexes, selection text, imagery databases for supplying visual attributes used to present the conditions). If such links are provided, a pseudo-relational database network is established.

Since values representing different conditions are stored, and not the graphical representations of such values, searching for certain conditions is easily performed through comparisons of values rather than "presentation specifics." Pixel level comparisons, which are commonplace with conventional systems, require considerable memory resources and significant time to execute. In contrast, value, or text-based, assessments are far simpler, whereas in the context of the present invention, each object record to be searched is evaluated by considering each regional field within the object record or, more preferably, considering only those regional fields objectively considered relevant.

Entering a search request can occur through comparing two like object records or through user-entry of a textual search term. Alternatively, the graphical user interface of this application could provide "search graphics," which visually resemble conditions (or potential conditions) assignable to an object. While certainly offering a simplified option for the user, the computer would be required to convert any search graphic input to a corresponding value, this value then takes the form of a user-made textual input and a search is performed in a manner consistent with the above general description.

Figure 7:
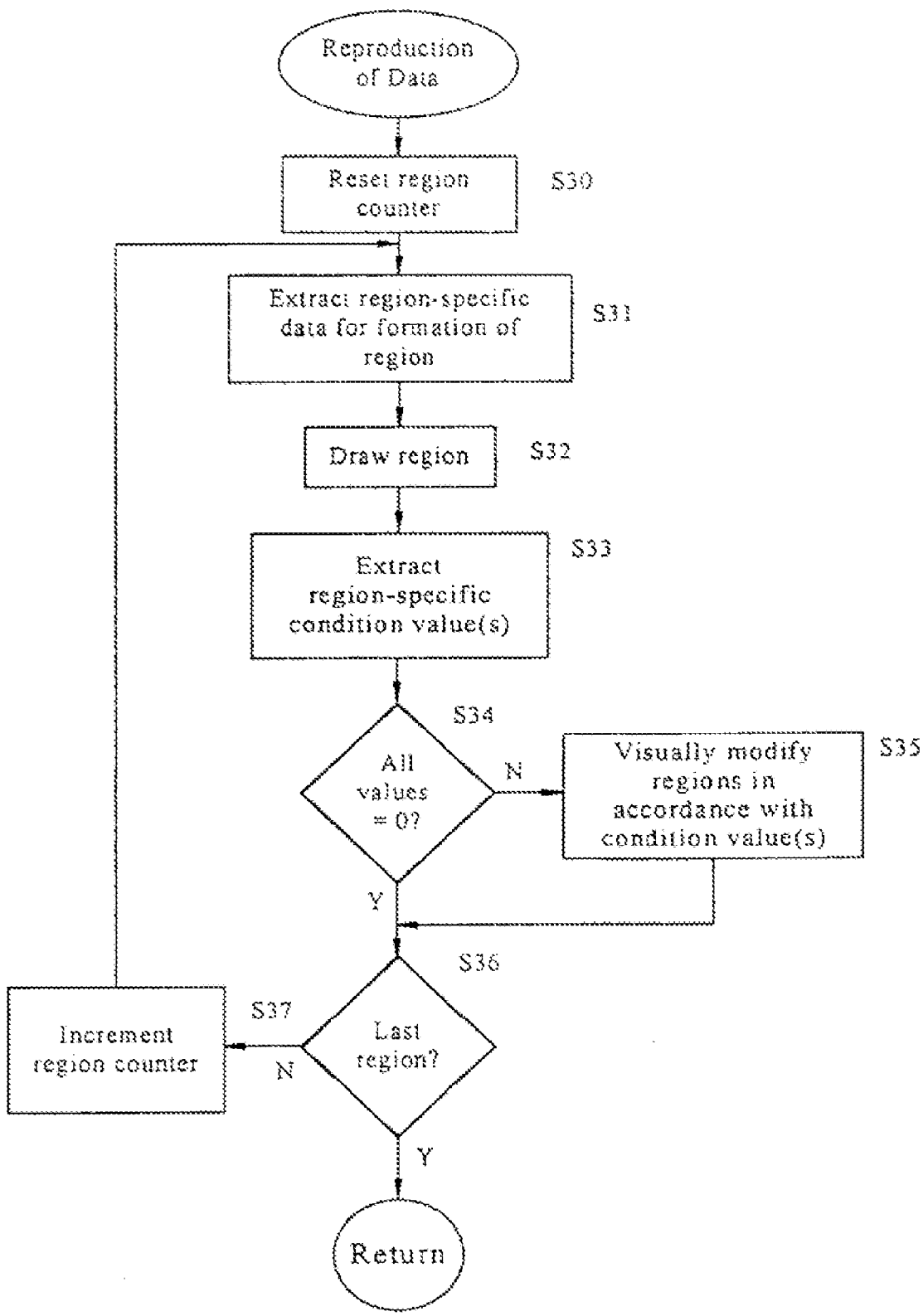
FIG. 7 is a routine to recall and assemble stored object data having assigned regional attributes.

FIG. 7 illustrates a routine for recalling and assembling stored data.

Once an object record has been properly identified and requested, a region counter is reset in Step S30. In Step S31, data for generating a region corresponding to the present region count is extracted from a memory of the computer, such data corresponding to, for example, a position within the object and a shape for the specific region. The subject region is positioned within the object in Step S32, this positioning typically takes the form of drawing the region within the object in accordance with the data extracted in Step S31. As the regions are reproduced, scaling or offsets, if any, are universally applied to each region. In Step S33, stored condition values are extracted. The values correspond to those conditions, if any, that were previously assigned to the specific region in accordance with the routine of FIG. 5.

After Step S33, the extracted values are assessed in the decision step of Step S34. If null values are identified (i.e., "0") and additional regions are required to be processed, the region counter is incremented in Step S37 and Steps S31-S34 are repeated. If values other than null values are identified in Step S34, the subject region is visually modified in accordance with the extracted condition value(s) in Step S35. When the last region is completed ("Y" in Step S36), the subroutine is completed.

The steps of FIG. 7 concern the presentation of an object having a single record that affects one or more of the regions of the object. However, if the object record includes multiple records (i.e., historical data that is distinguishable based on recording times), then a user will be provided an opportunity to select one of such records for display (e.g., "reference date" option 504 of FIG. 6). In furtherance of this concept, the steps of FIG. 7 can be further modified for an object possessing multiple records to automatically and sequentially present each of the records of the object. If multiple records correspond to different recording times, such sequential presentation would effect a "time lapse" illustration of any changes in the respective conditions attributed to the individual regions. In various applications, such comparative, historical presentations may offer some educational benefit.

As another preferred feature, whether at the time of attributing certain conditions to selected regions or at the time of recalling a previously defined object, a mechanism is provided to reveal those specific condition(s) assigned to any given region. As but one example, reference is made to FIG. 6.

When a pointer 512 is positioned relative to a specific region (or selected group of regions), pop-up information 506 can include previously selected conditions as well as non-stored details, for example, region boundaries, region positional values, normal conditions, and/or maximum-minimum value limits.

While the above description is directed to a basic system in accordance with the present invention, the following discussion is intended to describe such a system in the context of different operational environments. Of course, the following embodiments are not intended to limit the above description to only those few operational environments described.

FIRST EMBODIMENT

The disclosed system has application in the field of chronic pain management. In particular, the system would enable a user to consistently and effectively record at least subjective pain states.

Each data record corresponds to an individual patient. The "objects" include representations of the human body, and the "regions" are sub-regions of the bodily illustrations. Each record could contain one object or multiple objects. Importantly, common regions between like objects would maintain like designators (or region-specific characteristics).

Figure 8:
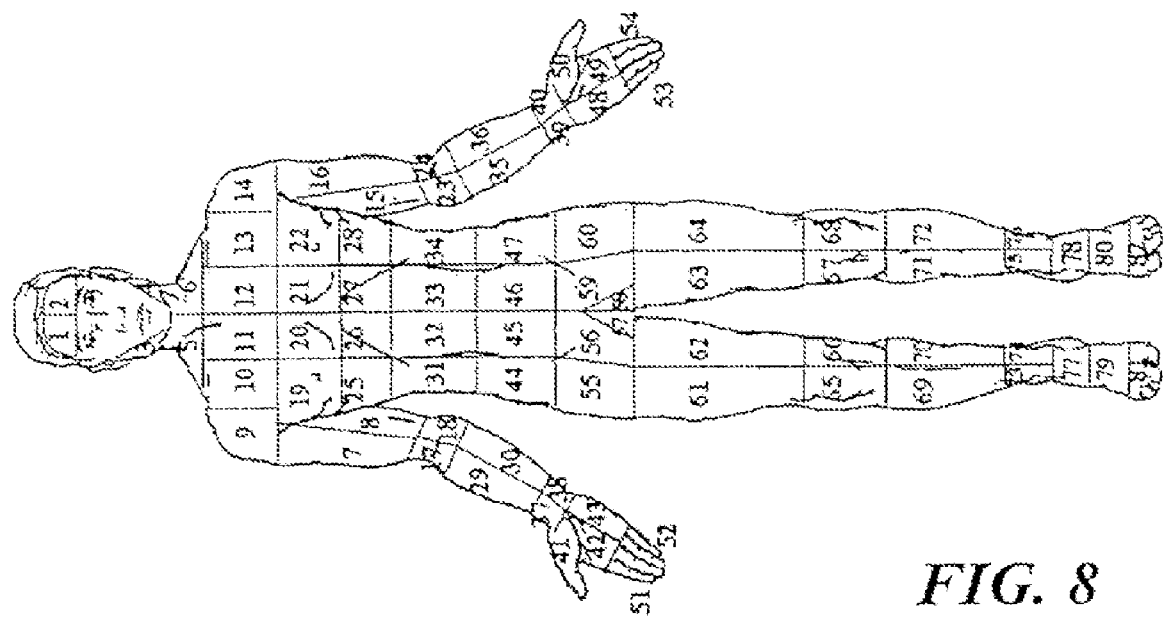
FIG. 8 is an anterior view of the object example of FIG. 4 in a prone orientation.
Figure 9:
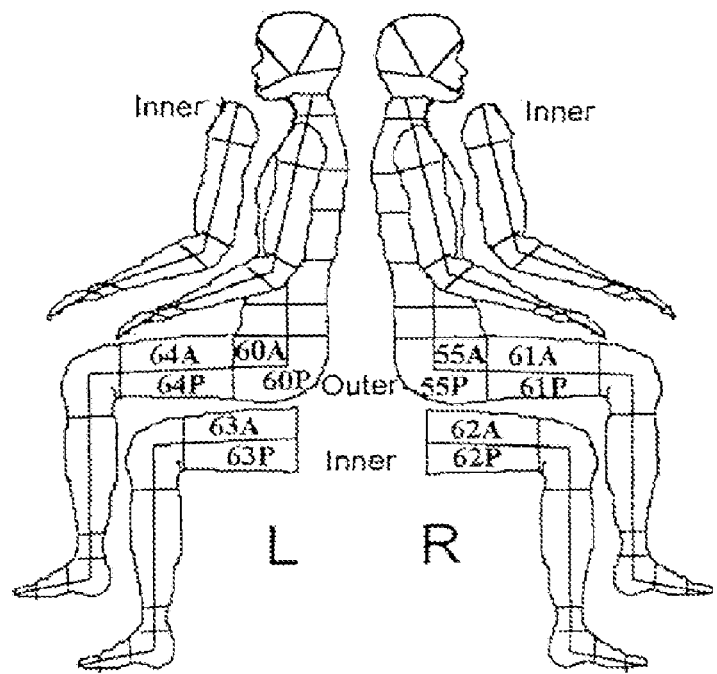
FIG. 9 is a side view of the object example of FIG. 4 in a sitting orientation.

Pain can substantially differ based on an orientation of the patient (e.g., standing, sitting). Possible objects for mapping are shown in FIG. 4, illustrating a posterior anatomical view of a human image in a standing position; FIG. 8, illustrating an anterior anatomical view of a human image in a prone position; and FIG. 9, illustrating side anatomical views of a human image in a seated posture. In regard to FIG. 9, given the two-dimensional orientation, it becomes necessary to provide exploded views to enable each of the applicable regions to be accessible for attributing values. While each of the above images is shown in two-dimensions, it is entirely appropriate that the user be presented three-dimensional images. In the preparation of any such three-dimensional images, it may be necessary to combine two objects (e.g., an anterior view of a subject and a posterior view of the subject).

Figure 2:
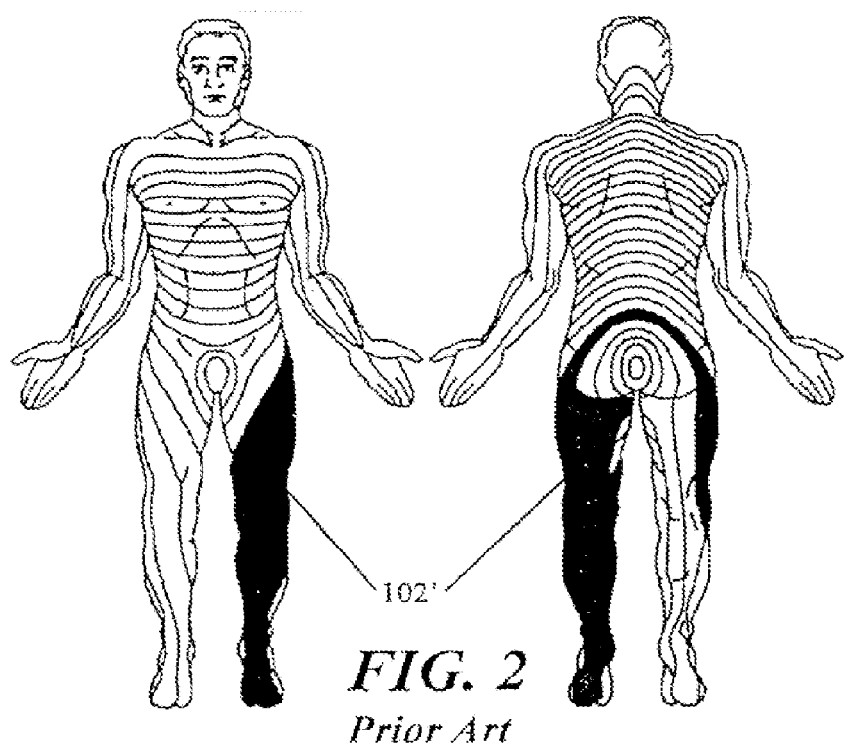
FIG. 2 illustrates a predetermined object, similar to that of FIG. 1, whereas the object is divided in accordance with recognized dermatomes.

The objects of FIGS. 4, 8, and 9, which appropriately illustrate only a portion of the total available regions, include a total of 164 regions—each anterior and posterior view including 82 regions. As discussed above, the number of regions is arbitrarily determined based on the object, the substantive information to be conveyed/represented by the regions, and the graphical manner used to convey relevant conditions assignable to the regions. Accordingly, a balance must be made between high resolution, which increases the number of regional records associated with each object and affects storage sizes and time overhead when handling, manipulating, or comparing such regional records, and low resolution, which may "dilute" the value of the substantive information to be conveyed/represented by an individual region (see FIG. 2).

For the present example, it has been found that 164 total regions provide sufficient resolution to enable any one region to be particularly associated with particular spinal nervous tissue. This association improves the chances that an effective therapy or treatment can be identified and administered. Notwithstanding, the number of regions should not be so excessive to hinder handling, manipulation, or comparison operations.

The "conditions" used to define the nature of the pain attributed to a specific region include: type, intensity, and depth. "Type" refers to a perceived character of the pain. "Intensity" refers to a perceived degree of pain. "Depth" refers to a perceived physical level of pain, i.e., surface to bone.

Figure 10:
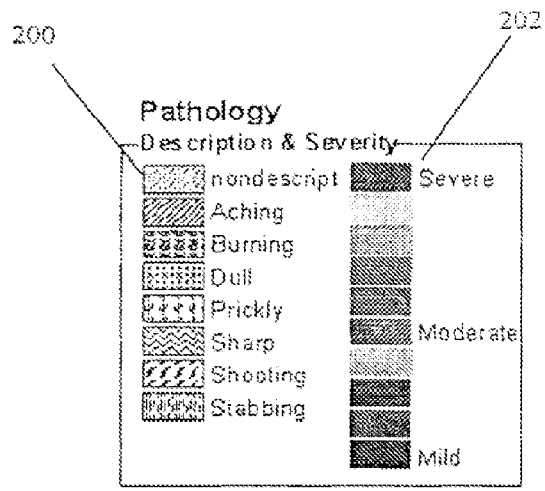
FIG. 10 illustrates one embodiment of definable attributes assignable to the regions of an object.

As it is intended that the attributes of any given region be readily discernable from only a visual inspection, the type, intensity, and depth attributes are given independent visual characteristics. For example, and consistent with the illustrations of FIG. 4 and the screen shot of FIG. 6, "type" is evidenced by a texture or pattern, and "intensity" is communicated by a change in color (e.g., hue, shade, etc.) "Depth" can be illustrated by shadowing a subject region to create the illusion a different physical level. FIG. 10 illustrates examples of patterns 200 and intensity coloration 202.

By providing each of the conditions with independent visual characteristics, the present invention can simultaneously convey each of the conditions attributed to any region. While the above discussion presents various options for defining certain pain characteristics and visually conveying such individual characteristics, one of ordinary skill in the art shall appreciate that these are but one example. To this end, the specific feature (e.g., colorization, pattern, etc.) used to convey a particular characteristic is not considered critical to the present invention. Rather, the present invention is more appropriately concerned with the broader concept of associating multiple conditions to a single region (or group of regions) and providing a graphical vehicle so that at least two of such conditions can be visibly discernable concurrently.

Figure 11:
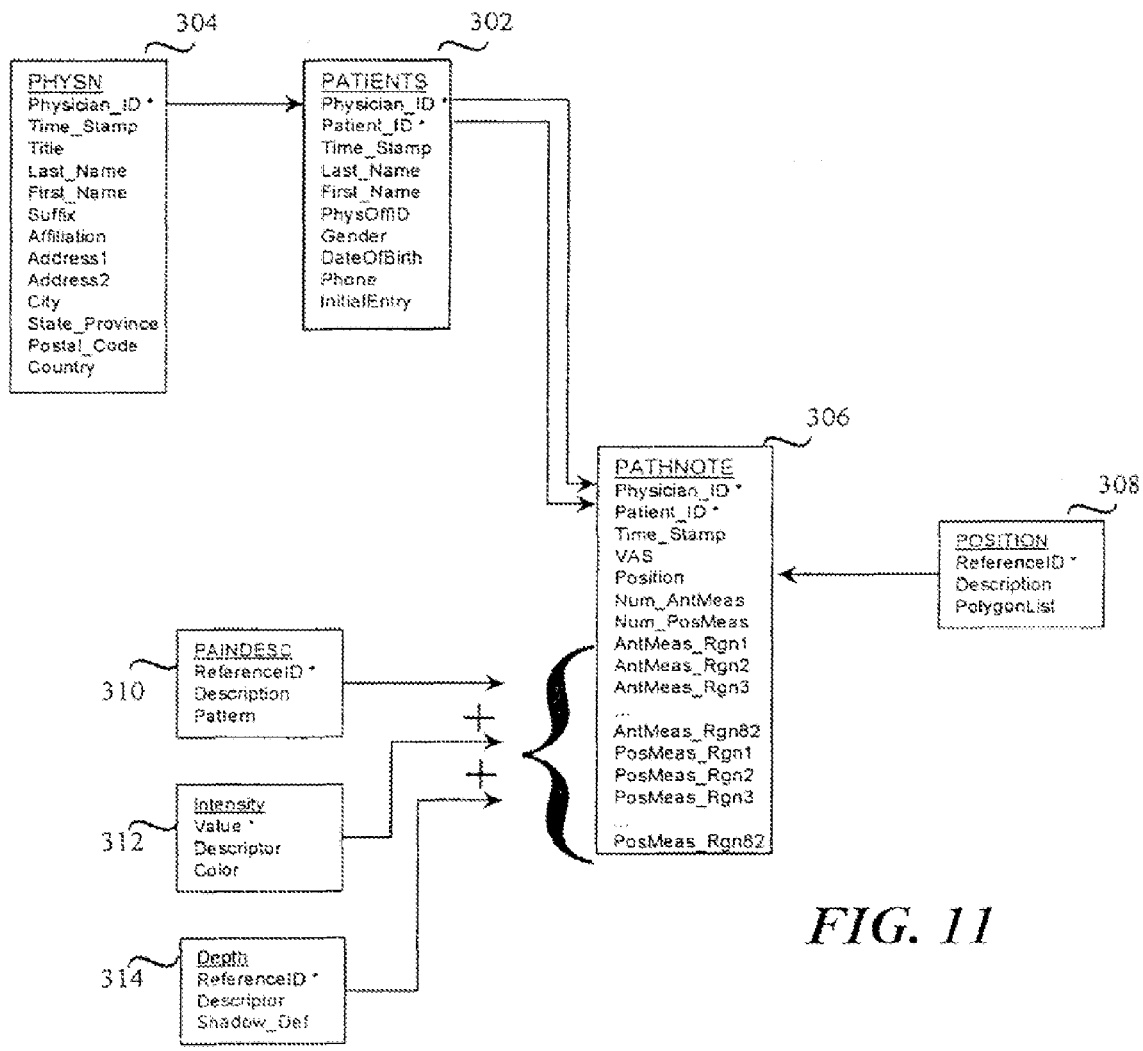
FIG. 11 illustrates an exemplary database structure.

In the specific context of this embodiment, FIG. 11 illustrates one example of a database structure. Relationships between database tables are designated by a "*". This illustration further includes representations of supporting links (or condition links) and objection condition fields.

As stated above, records for this embodiment are indexed in accordance with individual patients. Each record includes patient information (patient table 302), physician information (physician table 304), and pain map information (painmaps table 306).

In particular reference to the painmaps table 306, each pain map includes data that associates it with a patient, and for verification, the patient's physician. For maintaining historical records, each pain map is preferably date stamped at the time of creation. The "position" entry corresponds to the specific nature of the subject object. The mapping data for the subject object is contributed by the position table 308.

Each pain map further includes a plurality of fields that equally correspond to the number of available regions. In the illustrated example, "AntMeas_Rgn1" corresponds to region 1 of an anterior view of the object, while "PosMeas_Rgn1" corresponds to region 1 of a posterior view of such object. In accordance with the above discussion, each region is subject to receive condition values to particularly define any pain associated with that region. Accordingly, paindesc table 310, intensity table 312, and depth table 314 selectively function to assign respective values to the individual regional designations of each pain map table.

As described above in the context of the basic system, global conditions can be assigned to all regions of an object (Steps S11 and S12 of FIG. 5). For one example of such a "global condition," reference is now made to FIG. 4.

Element 402 represents a time-of-day continuum. The leftmost portion of the range represents early morning, and the right-most portion of the range represents night. By selecting a point along the continuum, a value is further added to each of the regional fields corresponding to a relative time associated with such static pain descriptions. While offering only one substantive example, it should be clear that a global condition could relate to either the patient's environment (e.g., element 402) and/or an underlying physical condition of the patient.

SECOND EMBODIMENT

While the first embodiment concerned mapping the entire human body, the second embodiment is more narrowly directed to the mapping of individual organs, for example, the heart or the brain. The present invention would enable organs, as objects, to be mapped for purposes of assigning conditions to the individual regions thereof. Depending upon the object, conditions could relate to characterizing conditions of necrosis, encephalopathy, stroke, cancer progression, or the like.

THIRD EMBODIMENT

Figure 12:
FIG. 12 is a plan view of another object example.

Unlike the first and second embodiments, the concept of the third embodiment is drawn to applying the database structure of the present invention to a non-human subject for regional data association and presentation. To this end, reference is made to FIG. 12.

The object, being a geographical body, is divided along natural boundary lines, i.e., county lines. The individual regions are capable of respectively receiving multiple conditions (e.g., population data, average income data, total rainfall data, average temperature data, etc.) that are specifically related to the individual regions. Moreover, in accordance with the present invention, each condition has associated therewith a unique graphical representation that is visually integrated into the object so as to readily convey the conditions, if any, associated with a given region.

The structure and functionality of the present invention is generally related to co-pending U.S. application Ser. No. 09/587,673, filed Jun. 5, 2000, now Pat. No. 6,690,397.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A system for managing patient data including a graphical database comprising:
    a computer system including a display, input controls, memory, and software, stored in the memory, for controlling the computer system, wherein the system comprises:
        (i) an object storage portion to store a predetermined object representation of an anatomical view of a patient;
        (ii) a mapping portion to extract the object representation from the object storage portion and to graphically subdivide the object representation into a plurality of regions, each region representing a data-input field;
        (iii) a selection portion adapted to allow selection of at least one region of a sub-divided object image; and
        (iv) an attribute assignment portion to assign conditions to selected regions, wherein the conditions include region-specific information and wherein each assigned condition defines a different type of pain experienced by the patient, each type of pain being independent of pain intensity,
    wherein each region is adapted to receive a plurality of conditions.

2. A system in accordance with claim 1, wherein each condition attributable to a selected region is graphically represented in a distinguishable manner after assignment by the user.

3. A system in accordance with claim 1, wherein the attribute assignment portion further effects of a graphical modification of any region subject to an assigned condition.

4. A system in accordance with claim 3, wherein depending on a condition assigned to a selected region, the attribute assignment portion changes a color of the selected region.

5. A system in accordance with claim 3, wherein depending on a condition assigned to a selected region, the attribute assignment portion applies a graphical pattern to the selected region.

6. A system in accordance with claim 3, wherein depending on a condition assigned to a selected region, the attribute assignment portion alters a dimensional perspective of the selected region relative to the object representation.

7. A system in accordance with claim 1, wherein each region includes a unique designation.

8. A system in accordance with claim 1, wherein each region is static in position and is independent of any overlapping regional boundaries of any adjacent regions.

9. A system in accordance with claim 1, wherein the system further comprises a conversion portion to convert graphical representations of regions and any assigned conditions into a non-graphical information form for storage.

10. A system in accordance with claim 9, wherein each region includes a unique designation, and the non-graphical information of each converted graphical representation of regions and any assigned conditions are formed into data records that are indexed in accordance with the unique designations.

11. A system in accordance with claim 10, wherein the system further comprises a comparison mechanism to compare one object representation to another like object representation,
    wherein the comparison mechanism is adapted to analyze data records for each object representation based on regional unique designations.

* * * * *